United States Patent [19]

Turesky et al.

[11] Patent Number: 5,250,288
[45] Date of Patent: Oct. 5, 1993

[54] METHOD FOR DESENSITIZING TEETH

[75] Inventors: Samuel S. Turesky, Brookline; Jean L. Spencer, Boston, both of Mass.

[73] Assignee: Gillette Canada, Inc., Trans, Canada

[21] Appl. No.: 8,524

[22] Filed: Jan. 25, 1993

Related U.S. Application Data

[60] Division of Ser. No. 820,348, Jan. 14, 1992, Pat. No. 5,211,939, which is a continuation-in-part of Ser. No. 759,535, Sep. 13, 1991.

[51] Int. Cl.$^5$ .......................... A61K 6/02; A61K 6/08; A61K 7/16
[52] U.S. Cl. ..................................... 424/49; 433/215; 433/217.1; 433/226; 433/228.1; 106/35; 15/159.1; 15/160; 15/167.1; 132/321
[58] Field of Search ..................... 424/49–58; 132/321; 106/35; 15/159.1, 160, 167.1

[56] References Cited

U.S. PATENT DOCUMENTS

| Re. 21,197 | 9/1939 | Hill et al. . |
|---|---|---|
| 2,304,478 | 12/1942 | Rosenzweig . |
| 2,558,992 | 7/1951 | Stott . |
| 2,994,642 | 8/1961 | Bossard . |
| 3,122,483 | 2/1964 | Rosenthal . |
| 3,226,297 | 12/1965 | Thuresson et al. . |
| 3,258,805 | 7/1966 | Rossnan . |
| 3,357,950 | 12/1967 | La Follette . |
| 3,357,951 | 12/1967 | Adams . |
| 3,380,848 | 4/1968 | Horowitz . |
| 3,450,813 | 6/1969 | Muhler . |
| 3,475,369 | 10/1969 | Blunt . |
| 3,542,519 | 11/1970 | Montalto . |
| 3,689,636 | 9/1972 | Svajda . |
| 3,772,431 | 11/1973 | Mlkvy et al. . |
| 3,810,479 | 5/1974 | Miles . |
| 3,863,006 | 1/1975 | Hodosh . |
| 3,888,976 | 6/1975 | Mlkvy et al. . |
| 3,934,001 | 1/1976 | Watson . |
| 3,956,480 | 5/1976 | Dichter et al. . |
| 3,957,968 | 5/1976 | Gordon . |
| 3,978,206 | 8/1976 | Naumann et al. . |
| 3,992,336 | 11/1976 | Faucher et al. . |
| 4,007,259 | 2/1977 | Patino et al. . |
| 4,011,309 | 3/1977 | Lutz . |
| 4,018,729 | 4/1977 | Faucher et al. . |
| 4,057,621 | 11/1977 | Pashley et al. . |
| 4,102,992 | 7/1978 | Davis . |
| 4,138,383 | 2/1979 | Rembaum et al. . |
| 4,155,870 | 5/1979 | Jorgensen . |
| 4,324,630 | 4/1982 | Sugita et al. ........................ 433/217.1 |
| 4,339,429 | 7/1982 | Raap et al. . |
| 4,348,378 | 9/1982 | Kosti . |
| 4,631,185 | 12/1986 | Kim . |
| 4,634,589 | 1/1987 | Scheller . |
| 4,678,814 | 7/1987 | Rembaum . |

(List continued on next page.)

FOREIGN PATENT DOCUMENTS 0079400 5/1983 European Pat. Off. .
WO90/10400 9/1990 World Int. Prop. O. .

OTHER PUBLICATIONS

Berman, J. Peridontal., 56:216 (1985).
Brännström and Astram, J. Dental Res., 43:619 (1963).
Gunji, Arch. Histo. J., 45:45–67 (1982).
Lecointre et al., J. Int. Med. Res., 14:217–222 (1986).
Närhi et al., Acte. Physiol. Scand., 115:173–178 (1982).
Pashley et al., Endodont. Dent. Traumatol, 3:80–82 (1987).
Pleasants et al., Oral Surg. Oral Med. Oral Pathol., 28:163–165 (1969).
Trowbridge, J. of Endodontics, 11:489–497 (1985).
Yoshiyama et al., J. Dent. Res., 69 (6):1293:1297 (1990).
Pashley et al., J. Prosthet. Dent., 53 (4):511–516 (1985).

*Primary Examiner*—Shep K. Rose
*Attorney, Agent, or Firm*—Fish & Richardson

[57] ABSTRACT

A method for desensitizing teeth includes applying an effective amount of charged polymeric particles to the surface of the tooth.

16 Claims, 1 Drawing Sheet

U.S. PATENT DOCUMENTS

| | | |
|---|---|---|
| 4,685,883 | 8/1987 | Jernberg . |
| 4,710,372 | 12/1987 | Scheller . |
| 4,751,072 | 6/1988 | Kim . |
| 4,762,373 | 8/1988 | Amos et al. .......................... 300/21 |
| 4,780,320 | 10/1988 | Baker . |
| 4,802,255 | 7/1988 | Breuer et al. . |
| 4,867,988 | 9/1989 | Chernack . |
| 4,892,736 | 1/1990 | Goodson . |
| 4,904,479 | 2/1990 | Illum . |
| 4,911,922 | 3/1990 | Masuhara et al. . |
| 4,919,939 | 4/1990 | Baker . |
| 4,959,220 | 9/1990 | Yamamoto et al. . |
| 4,963,347 | 10/1990 | Humphries et al. . |
| 4,978,391 | 12/1990 | Jones . |
| 4,980,150 | 12/1990 | Keith . |
| 4,986,288 | 1/1991 | Kent et al. . |
| 4,990,327 | 2/1991 | Neirinckx . |
| 4,992,258 | 2/1991 | Mason . |
| 5,000,941 | 3/1991 | Chernack . |
| 5,037,818 | 8/1991 | Sime .................................. 514/183 |
| 5,061,106 | 10/1991 | Kent . |
| 5,141,290 | 8/1992 | Mairon . |
| 5,185,155 | 2/1993 | Behan et al. ...................... 424/251 |

METHOD FOR DESENSITIZING TEETH

This is a divisional of copending application Ser. No. 07/820,348, filed Jan. 4, 1992, now U.S. Pat. No. 5,211,939, which is a continuation-in-part of U.S. Ser. No. 07/759,535, filed Sep. 13, 1991.

BACKGROUND OF THE INVENTION

The invention relates to desensitizing teeth.

The dentin layer in a tooth generally contains channels, or tubules, extending from the pulpal surface to the peripheral surface located interior to the enamel and cementum. Exposure of these tubules in the dentin may occur through the loss of enamel and/or gingival recession accompanied by a loss of cementum. It has been theorized that these exposed tubules are in part responsible for the hypersensitivity to external stimuli, such as hot or cold fluids, or applied mechanical pressures often exhibited by teeth.

The problem of hypersensitive teeth is well-recognized, and various treatments have been proposed in the art. Pashley et al., U.S. Pat. No. 4,057,021, describes desensitizing hypersensitive teeth by applying an aqueous solution of alkali metal salts and ammonium oxalate to the surface of the teeth. Kim, U.S. Pat. Nos. 4,631,185 and 4,751,072, describes desensitizing teeth by treatment with potassium salts. Neirinckx, U.S. Pat. No. 4,990,327, describes desensitizing teeth with strontium ion and fluoride ion. Mason, U.S. Pat. No. 4,992,258, describes desensitizing teeth by applying a dentifrice including a montmorillonite clay. Lutz, U.S. Pat. No. 4,011,309, describes a desensitizing dentifrice composition that includes citric acid, sodium citrate, and non-ionic polyol surfactant. Mlkvy et al., U.S. Pat. Nos. 3,888,976 and 3,772,431 describe using a zinc or strontium ion containing astringent-desensitizing agent in an effervescent mouthwash tablet. Hodosh, U.S. Pat. No. 3,863,006, describes desensitizing teeth with a nitrate salt. Svajda, U.S. Pat. No. 3,689,636, describes desensitizing teeth with solutions of chloride salts. Rosenthal, U.S. Pat. No. 3,122,483, describes desensitizing teeth with strontium ions. Scheller, U.S. Pat. Nos. 4,634,589 and 4,710,372, describe a dentifrice containing apatite particles for treating hypersensitive teeth.

It is known that dentifrices may include particles which thicken or color the dentifrice, or which make the dentifrice abrasive. For example, in Scheller '589 and '372, the apatite particles are included in the dentifrice to roughen the surface of the teeth. See also, Thuersson et al., U.S. Pat. No. 3,226,297 (e.g., col. 4, lines 34-43); Blunt, U.S. Pat. No. 3,475,369 (e.g., col. 12, lines 27-34); Patino et al., U.S. Patent No. 4,007,259 (e.g. col. 1, line 30); Bossard, U.S. Pat. No. 2,994,642 (e.g., col. 4, lines 40-60); La Follette, U.S. Pat. No. 3,357,950 (e.g., col. 1, lines 50-61); Adams, U.S. Patent No. 3,357,951 (e.g., col. 1, lines 49-61); Muhler, U.S. Pat. No. 3,450,813; Watson, U.S. Pat. No. 3,934,001; Naumann et al., U.S. Pat. No. 3,978,206 (e.g., col. 1, lines 39-57); Davis, U.S. Pat. No., 4,102,992; and Humphries et al., U.S. Pat. No. 4,963,347.

Jernberg, U.S. Pat. No. 4,685,883, describes using biodegradable microspheres to deliver chemotherapeutic agents to lesions in the gums.

Dichter et al., U.S. Pat. No. 3,956,480 describes treating teeth with anionic polymers complexed with a cationic germicide, such as chlorhexidine.

SUMMARY OF THE INVENTION

In one aspect, the invention features a method of desensitizing a hypersensitive tooth by applying an effective amount of charged polymeric particles to the surface of the tooth. Charged, as used herein, means that the particles have an average surface charge density of at least 0.5 $\mu C/cm^2$ (microcoulomb per square centimeter) as measured by conductiometric titration.

In another aspect, the invention features a method of treating a hypersensitive tooth that has exposed tubules in the dentin layer of the tooth. The method includes applying a sufficient amount of charged polymeric particles to the surface of the tooth to block the tubules.

The preferred particles have an average size of between 0.01 micron to 3 microns, more preferably between 0.2 micron to 0.6 micron, and an average surface charge density of greater than $4\mu C/cm^2$. The more preferred particles are microspheres, such as the polystyrene microspheres described in U.S. Ser. No. 07/759,535, filed Sep. 13, 1991, which is assigned to the same assignee as the present application and is hereby incorporated by reference herein; the more preferred particles, optionally, may have an antimicrobial (e.g., chlorhexidine) an analgesic compound (e.g. barbital), or other therapeutic substance (e.g. anti-calculus agent or anti-caries agent), adsorbed on their surface, e.g., as described in U.S. Ser. No. 07/759,535. In a preferred method, the surface of the hypersensitive tooth is polished, and a dispersion of the particles is applied to the polished surface for at least one minute. A preferred method of applying the particles is by brushing the teeth with a toothbrush having bristles which include the particles.

In another aspect, the invention features a method of treating hypersensitive teeth by applying charged polymeric microspheres to the surface of the tooth.

In another aspect, the invention features a dentifrice including charged polymeric microspheres.

The invention provides an effective, straightforward way to desensitize teeth. Without being bound to any theory, it is believed that the invention is effective at least in part because the charged particles cling to the surface of the teeth, blocking the tubules, and making it more difficult for external stimuli like hot or cold temperatures to affect the nerve in the pulp. When some of the particles blocking the tubules eventually wash out of the tubules, they are easily replenished by an additional application of particles.

Other features and advantages of the invention will be apparent from the description of the preferred embodiment thereof, and from the claims.

DESCRIPTION OF THE PREFERRED EMBODIMENT

The charged particles preferably have an average diameter of less than 0.6 micron. Larger particles may not fit as well in the dentin tubules.

The more preferred particles are positively charged polystyrene microspheres having an average diameter of about 0.5 micron. The microspheres were supplied by Interfacial Dynamics Corp. of portland, Oregon (Catalog No. 10-43-57). It is believed that to provide the benefits of the invention a sufficient quantity of charged particles should be applied to the surface of a hypersensitive region of the tooth so that the charged particles clog the exposed tubules in the dentin. This application can be performed in a variety of ways; for example, the tooth surface can be washed with a concentrated aqueous dispersion of the particles. Generally, the more concentrated the dispersion of particles, the less time the surface of the tooth needs to be washed. The following are examples of typical procedures that can be used to apply the particles.

Figure 1:
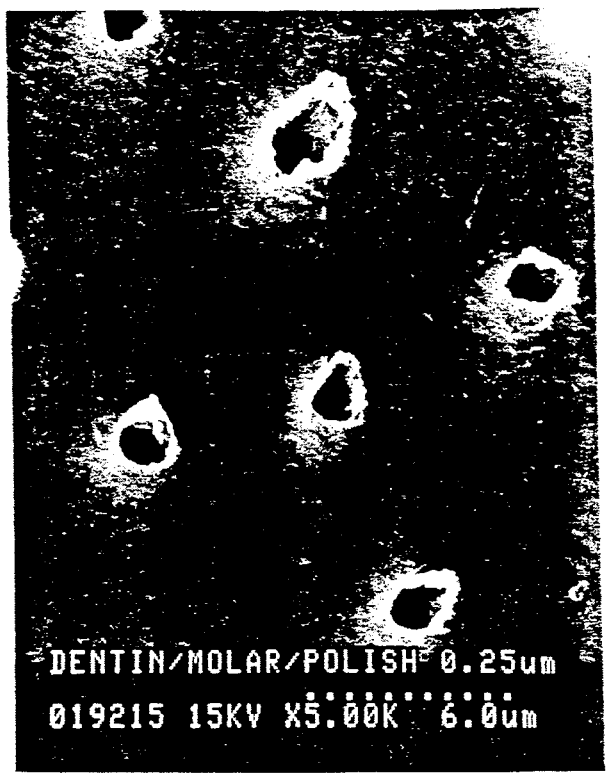
FIG. 1 is an electron micrograph of a dentin surface prior to exposure to the particles of the invention.
Figure 2:
FIG. 2 is an electron micrograph of the surface of FIG. 1 after exposure to the particles of the invention.

The tooth surface initially is polished. The surface is then exposed to an aqueous dispersion of the more preferred microspheres ($1.6 \times 10^{10}$ particles/ml, pH 4). A preferred dispersion is formed by diluting 916 $\mu$l of the preferred microsphere dispersion (Catalog No. 10-43-57, Interfacial Dynamics) to a volume of 40 ml with water which has been filtered, double distilled, and adjusted to pH 4. The dispersion is then agitated against the tooth surface for 5 minutes. Alternatively, the surface is exposed to a pressurized jet of the aqueous dispersion e.g., at a pressure of about 30 psi for about 20 seconds, or the surface is brushed with bristles that are saturated with microspheres, for 3 minutes; the saturated bristles are prepared as described in U.S. Ser. No. 759,535. Each of these procedures, when performed on a tooth that had been removed from the mouth, was effective at blocking the exposed tubules in the dentin of the tooth with the microspheres, as confirmed by scanning electron microscope. FIGS. 1 and 2 show the dentin surface, before and after, respectively, a 5 minute exposure to a latex particle dispersion of 0.489 $\mu$m positively charged polystyrene microspheres. Prior to exposure to the dispersion, the exposed tubules in the dentin are empty; after exposure they are substantially filled with the particles present in the dispersion. (FIGS. 1 and 2 were both taken at 5000x magnification.)

An alternative procedure for applying the particles to the tooth is to soak a cotton pellet with an aqueous dispersion of the particles, and then rub the cotton pellet over the polished surface of the tooth, preferably for one minute or less.

Other embodiments are within the claims. For example, other types of charged microspheres, such as those described in U.S. Ser. No. 759,535, can be used in place of the polystyrene microspheres. Moreover, the microspheres can be included in a dentifrice (toothpaste) or a mouthwash; when the dentifrice or mouthwash contacts the surface of a tooth the microspheres will fill in the tubules. This approach can be used, in particular, to replenish microspheres that were previously blocking a tubule but have, to some extent, washed out of the tubule over time. If a mouthwash is used, it may be applied under pressure, using any commercially available water-jet appliance. The microspheres can also be applied, for example, by including them on the bristles of toothbrushes or on dental floss, as described in U.S. Ser. No. 759,535. While the times, pressures and other conditions given above were preferred in a laboratory setting, these conditions may be varied as desired to adapt them to a clinical setting, provided the time, pressure etc., is adequate to block the tubules. Effective conditions may be readily determined by those skilled in the art, e.g. by determining whether a patient's tooth is still sensitive after the treatment.

In addition, the particles may have an antimicrobial, analgesic or other therapeutic substance adsorbed on their surface, e.g., as described in U.S. Ser. No. 759,535. These particles provide both the desensitization benefit of this invention and the anti-microbial benefit described in U.S. Ser. No. 759,535 or other benefit provided by the therapeutic agent selected.

We claim:

1. A method of desensitizing a hypersensitive tooth, comprising applying an effective amount of charged polymeric particles to the surface of said tooth to cause desensitization of said tooth.

2. The method of claim 1 wherein said particles have an average diameter of 0.01 micron to 3 microns.

3. The method of claim 2 wherein said particles have an average diameter of 0.2 micron to 0.6 micron.

4. The method of claim 1 wherein said particles have an average surface charge density of greater than $4\mu C/cm^2$.

5. The method of claim 1 wherein said particles are positively charged.

6. The method of claim 1 wherein said particles are applied in the form of an aqueous dispersion.

7. The method of claim 6, further comprising polishing said surface of said tooth prior to applying said aqueous dispersion.

8. The method of claim 6, wherein said particles are applied to said surface for less than about one minute.

9. A method of desensitizing a hypersensitive tooth, said tooth comprising an exposed tubule in the dentin layer of said tooth, said method comprising applying to said surface of said tooth a sufficient amount of charged polymeric particles to block said tubule.

10. The method of claim 9 wherein said particles have an average diameter of less than 3 microns.

11. The method of claim 10 wherein said particles comprise microspheres.

12. The method of claim 11 wherein said microspheres comprise polystyrene.

13. A method of treating a hypersensitive tooth, comprising applying charged polymeric microspheres to the surface of said tooth.

14. The method of claim 13 wherein said microspheres are positively charged.

15. The method of claim 11 wherein said microspheres comprise polystyrene.

16. The method of claim 13 wherein said particles are applied by brushing the tooth with a toothbrush having bristles which include the particles.

* * * * *